US012605281B1

(12) United States Patent
Mazaheri

(10) Patent No.: US 12,605,281 B1
(45) Date of Patent: Apr. 21, 2026

(54) EPITHELIAL REMOVAL TOOL WITH LIGHT EMITTER AND METHOD FOR AN OPHTHALMIC SURGICAL PROCEDURE

(71) Applicant: Mehrdad Mazaheri, Richardson, TX (US)

(72) Inventor: Mehrdad Mazaheri, Richardson, TX (US)

( * ) Notice: Subject to any disclaimer, the term of this patent is extended or adjusted under 35 U.S.C. 154(b) by 356 days.

(21) Appl. No.: 16/679,073

(22) Filed: Nov. 8, 2019

Related U.S. Application Data

(63) Continuation-in-part of application No. 16/010,467, filed on Jun. 17, 2018, now abandoned.

(51) Int. Cl.
| | |
|---|---|
| *A61F 9/013* | (2006.01) |
| *A61B 90/30* | (2016.01) |
| *A61B 17/32* | (2006.01) |

(52) U.S. Cl.
CPC .............. *A61F 9/013* (2013.01); *A61B 90/30* (2016.02); *A61B 17/320068* (2013.01); *A61B 2090/306* (2016.02)

(58) Field of Classification Search
CPC .... A61F 9/013; A61B 90/30; A61B 2090/306
See application file for complete search history.

(56) References Cited

U.S. PATENT DOCUMENTS

| | | | | |
|---|---|---|---|---|
| 4,834,748 | A | * | 5/1989 | McDonald .............. A61F 9/013 |
| | | | | 606/166 |
| 5,312,330 | A | * | 5/1994 | Klopotek ................ A61F 9/013 |
| | | | | 604/521 |
| 5,649,943 | A | * | 7/1997 | Amoils ................... A61F 9/013 |
| | | | | 606/166 |
| 5,658,148 | A | * | 8/1997 | Neuberger ............. A61N 5/062 |
| | | | | 433/29 |
| 5,699,810 | A | * | 12/1997 | Pallikaris ................ A61F 9/013 |
| | | | | 128/898 |
| 5,792,160 | A | * | 8/1998 | Weiss ...................... A61F 9/013 |
| | | | | 606/166 |
| 5,813,855 | A | * | 9/1998 | Crisio, Jr. .......... A46B 15/0036 |
| | | | | 433/29 |
| 6,056,548 | A | * | 5/2000 | Neuberger ........... A61C 19/066 |
| | | | | 433/215 |
| 6,132,421 | A | * | 10/2000 | Clapham ............. A61F 9/00804 |
| | | | | 606/4 |
| 6,290,496 | B1 | * | 9/2001 | Azar .................... A61N 5/0603 |
| | | | | 433/29 |

(Continued)

*Primary Examiner* — Phong Son H Dang

(57) ABSTRACT

An epithelial removal tool and epithelial surgical procedure emits light from a lower end of the removal tool to provide a fixation light, a point for the patient to focus on to prevent eye movement and avoid injury during ophthalmic surgery. The removal tool has a housing which secures one or more removal members in fixed position. The removal members are preferably provided by synthetic brush bristles. One or more optical fibers extend from an upper portion of the housing, through the brush bristles, and to the light region which provides a fixation point that is centrally located on the terminal end of the bristles and on the bottom of the removal tool. In some embodiments, rather than a brush the removal tool may be in solid form, preferably provided by a pliant member formed of a polymeric material which transmits sufficient light to provide a fixation point.

16 Claims, 13 Drawing Sheets

(56)                    References Cited

U.S. PATENT DOCUMENTS

| | | | | |
|---|---|---|---|---|
| 6,623,272 | B2 * | 9/2003 | Clemans | A46B 15/0002 433/215 |
| 7,004,953 | B2 * | 2/2006 | Pallikaris | A61F 9/013 606/166 |
| D557,416 | S * | 12/2007 | Wang | D24/152 |
| 8,522,383 | B2 * | 9/2013 | Hulli | A46B 3/06 15/28 |
| 2004/0019990 | A1 * | 2/2004 | Farrell | A61C 17/22 134/1 |
| 2004/0053190 | A1 * | 3/2004 | Lin | A61N 5/0603 433/29 |
| 2004/0191729 | A1 * | 9/2004 | Altshuler | A46B 15/0002 433/29 |
| 2005/0050659 | A1 * | 3/2005 | Chan | A46B 15/0036 433/29 |
| 2005/0288696 | A1 * | 12/2005 | Pallikaris | A61F 9/013 606/166 |
| 2007/0015112 | A1 * | 1/2007 | Hochman | A61B 8/546 433/215 |
| 2008/0131834 | A1 * | 6/2008 | Shepherd | A46B 15/0034 433/29 |
| 2008/0256729 | A1 * | 10/2008 | Link | A46B 15/0034 15/105 |
| 2008/0276393 | A1 * | 11/2008 | Russell | A61N 5/0624 15/105 |
| 2008/0286713 | A1 * | 11/2008 | Nanda | A46D 1/00 15/207.2 |
| 2009/0083924 | A1 * | 4/2009 | Shepherd | A46B 15/0002 15/105 |
| 2010/0100030 | A1 * | 4/2010 | Driscoll | A61Q 3/00 514/561 |
| 2011/0152979 | A1 * | 6/2011 | Driscoll | A61N 5/0624 607/93 |
| 2011/0296643 | A1 * | 12/2011 | Shepherd | A61N 5/0603 15/167.1 |
| 2012/0087970 | A1 * | 4/2012 | Newman | A61K 9/0051 514/251 |
| 2013/0019423 | A1 * | 1/2013 | Srutkowski | G02B 6/3807 15/207.2 |
| 2013/0086758 | A1 * | 4/2013 | Boutoussov | A61C 17/222 15/22.1 |
| 2013/0089829 | A1 * | 4/2013 | Boutoussov | A61C 19/06 433/29 |
| 2015/0283401 | A1 * | 10/2015 | Cha | A46D 1/0207 433/29 |
| 2015/0366709 | A1 * | 12/2015 | Roholt | A61F 9/00709 606/161 |
| 2016/0038762 | A1 * | 2/2016 | Lin | A61N 5/0603 433/29 |
| 2016/0286948 | A1 * | 10/2016 | Amron | A46D 1/0207 |
| 2017/0020277 | A1 * | 1/2017 | Barnes | A46B 15/0034 |
| 2017/0112603 | A1 * | 4/2017 | Lee | A46B 11/00 |
| 2018/0317640 | A1 * | 11/2018 | Schär | B29C 45/2626 |

* cited by examiner

EPITHELIAL REMOVAL TOOL WITH LIGHT EMITTER AND METHOD FOR AN OPHTHALMIC SURGICAL PROCEDURE

CROSS-REFERENCE TO RELATED APPLICATION

The present application is related to, as a continuation-in-part, to U.S. application Ser. No. 16/010,467, filed Jun. 17, 2018 and entitled "Epithelial Removal Tool with Light Emitter," invented by Mehrdad Mazaheri, inventor of the present application.

TECHNICAL FIELD OF THE INVENTION

The present invention relates in general to a method and an apparatus for removing corneal, epithelial tissue, and in particular to a tool for abrading tissue using rotary motion, and in some embodiments sonic and ultrasonic energy.

BACKGROUND OF THE INVENTION

Ophthalmic surgeons frequently use tools for removing corneal, epithelial tissue using abrasion techniques. Examples of such tools are shown in U.S. Pat. No. 5,649, 943, entitled "Ophthalmic Treatment Apparatus And Its Use," and invented by Amoils, and U.S. Patent Publication No. 2015/0366709, entitled "Ophthalmic Treatment Apparatus," and invented by Roholt, which are hereby incorporated by reference as if fully set forth herein. Both patents describe epithelial removal tools provided by brushes having bristles which are moved over a patients's eyes to remove epithelial tissue for procedures such as LASIK surgery. Typically a fixture holds a patient's eyelid open and then the patient is required to hold his eye in a stationary position during the procedure, as the epithelial removal tool is used to remove the epithelial tissue. However, when brushes are used such as that disclosed in the above-referenced patent publications, patients can only see the black of the brush bristles obscuring their field of view and do not have a single point or region on which to focus their eyes. This regularly results in patients moving their eyes during the procedure, risking injury and larger than needed epithelial removal. Larger than needed epithelial removal may lead to healing difficulties, healing times of weeks rather than one or two days, and higher chances of post surgery scarring and regression.

SUMMARY OF THE INVENTION

An epithelial removal tool with light emitter and method for using the epithelial removal tool are disclosed for use in ophthalmic surgical procedures. An epithelial removal tool emits light from a central region on the bottom of the tool which provides a fixation light, providing a point for the patient to focus on to prevent eye movement. The removal tool has a housing which secures removal members in fixed position. The removal members are preferably provided by synthetic brush bristles, as is well known in the current art. One or more optical fibers extend from the housing, through the brush bristles, and to a light region located within the terminal end of the bristles and on the bottom of the tool. In a first embodiment, a light source is located within the housing and powered by an internal battery. In a second embodiment, the light source located in the housing is powered by induction using a power supply external from the housing and the removal tool. In a third embodiment the light source is external from the housing and the tool and transmits light to a collector which is mounted to the housing and coupled to one or more optical fibers.

DESCRIPTION OF THE DRAWINGS

For a more complete understanding of the present invention and the advantages thereof, reference is now made to the following description taken in conjunction with the accompanying Drawings in which

FIG. 1 is a front, elevation view of a hand-held motor unit being used to power an epithelial removal tool with a light emitter during ophthalmic surgery;

FIG. 2 is perspective view of a first embodiment of an epithelial removal tool with a light emitter;

FIG. 3 is a section view of the removal tool, taken along section line 3-3 of FIG. 2;

FIG. 4 is a section view of a second embodiment of an epithelial removal tool with a light emitter having an external power source, as would be viewed when taken along section line 3-3 of FIG. 2;

FIG. 5 is a section view of a third embodiment of an epithelial removal tool with a light emitter having an external light source, as would be viewed when taken along section line 3-3 of FIG. 2;

FIG. 6 is a bottom view showing the lower end of an epithelial removal tool with a light emitter, and depicting a central region from which the light is emitted generally as a point;

FIG. 7 is a bottom view showing the lower end of an epithelial removal tool with a light emitter, and depicting a central region from which the light is emitted generally as a circular shaped region;

FIG. 8 is a section view of a fourth embodiment of an epithelial removal tool with a light emitter, as would be viewed when taken along section line 3-3 of FIG. 2, and showing a single removal member formed of a solid material which protrudes from the housing;

FIG. 9 is a section view of a fifth embodiment of an epithelial removal tool with a light emitter, as would be viewed when taken along section line 3-3 of FIG. 2, and showing a single removal member in which the light source is located in the hand-held motor unit and light is passed through the drive stem which extends into the removal tool housing;

FIG. 10 is a section view of a sixth embodiment of an epithelial removal tool having a light emitter which provides a fixation point, as would be viewed when taken along section line 3-3 of FIG. 2;

FIG. 11 is a section view of the epithelial removal tool of FIG. 10, taken along section line 11-11;

FIG. 12 is a section view of a seventh embodiment of an epithelial removal tool having the same components as the epithelial removal tool of FIGS. 10 and 11, except that the removal member is formed of a single, pliant polymeric material; and FIG. 13 is a flow chart depicting a process for removal of epithelial material using one of the removal tools with light emitters according to the present invention.

DETAILED DESCRIPTION OF THE INVENTION

Figure 1:
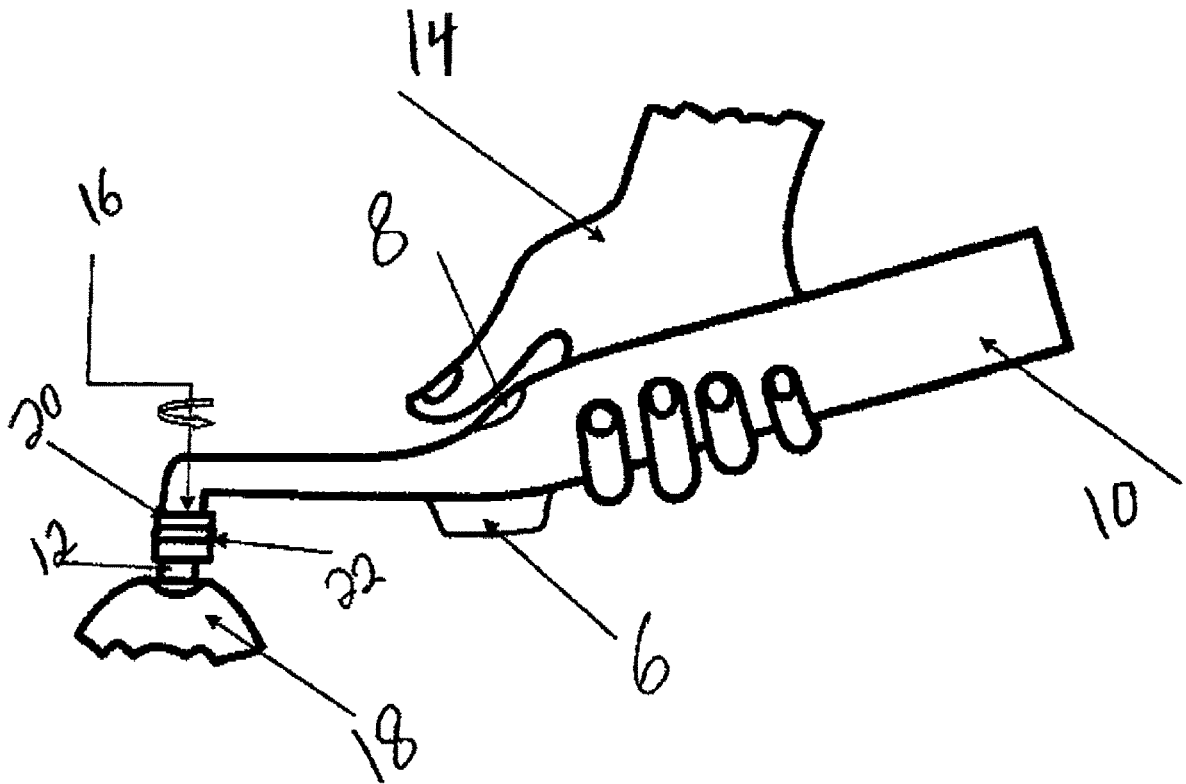
FIGS. 1 through 13 show various aspects for an epithelial removal tool with a light emitter and method for using the removal tool with light emitter to provide a fixation point for a patient undergoing an ophthalmic surgical procedure to remove tissue from an epithelial lawyer of an eye according to the present disclosure, as set forth below.
Figure 3:
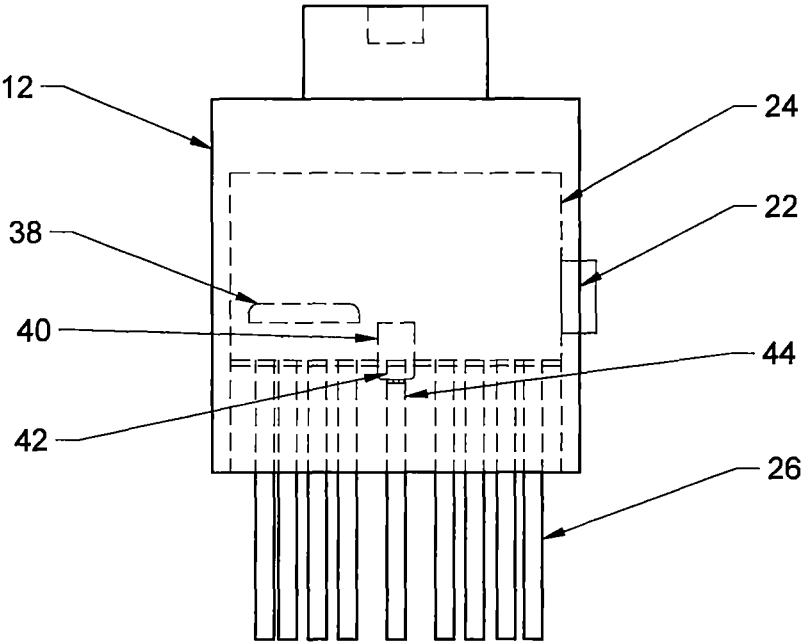
Figure 4:
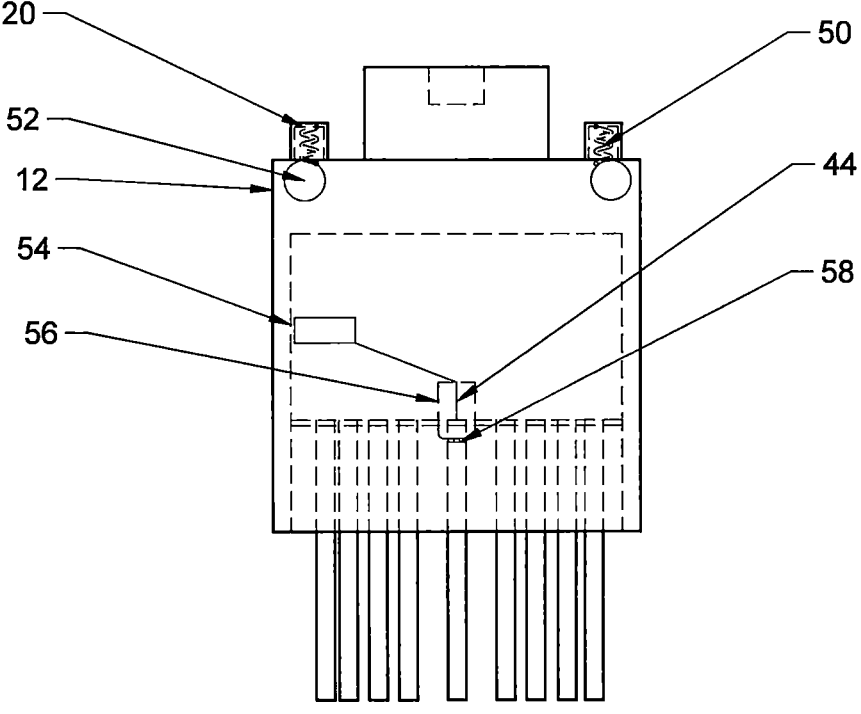
Figure 5:
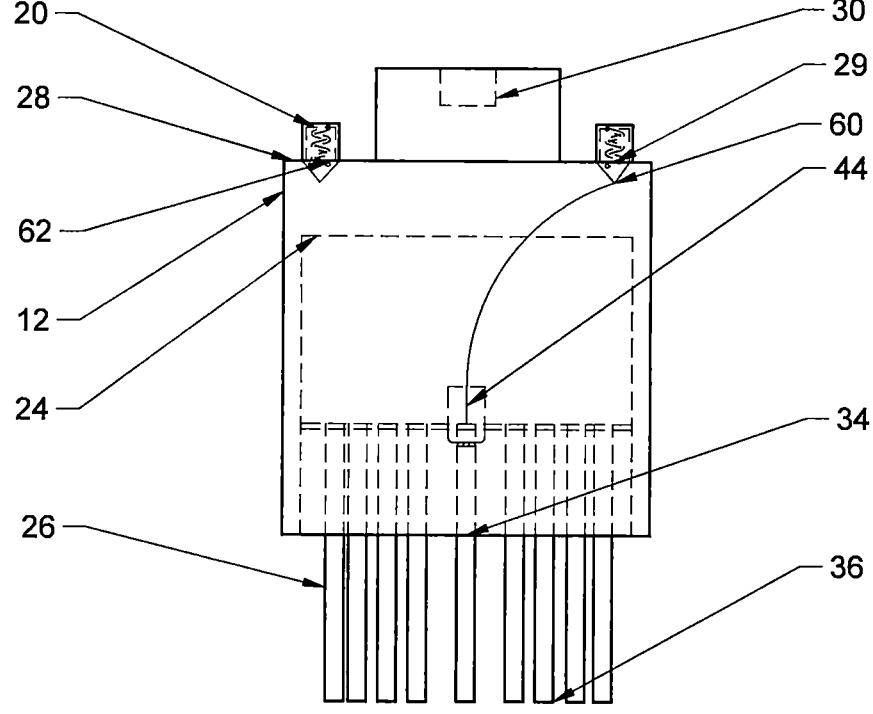

Referring to the Figures, FIG. 1 is a front, elevation view of a hand-held motor unit 10 being used during ophthalmic surgery to power an epithelial removal tool 12 having a light emitter. A surgeon is holding the motor unit 10 which is rotating the removal tool 12 about the axis 16. Depending upon operation of the hand-held motor unit 10, the removal tool 12 is powered with rotary motion about the axis 16, and may also be powered with reciprocating rotary motion, vibratory motion and ultrasonic motion. A switch 6 is provided for powering the motor unit 10 on and off, and may be pressed to operate the motor unit 10 for a fixed period of time, such as 60 seconds, and then the motor unit 10 will automatically shut off. A thumb switch 8 is also provided which provides variable speed for the motor unit 10. A switch 22 is shown as part of the removal tool 12 for applying power to an internal light source 40 which is shown in FIG. 3. A transmitter adapter 20 is shown mounted to the end of the hand-held motor unit 10. In the embodiment of FIG. 4 the transmitter adapter 20 will transmit EMF as magnetic fields to power an internal light source mounted in the removal tool 12 by means of induction. In the embodiment of FIG. 5 the transmitter adapter 20 will transmit EMF as light to provide a light source for the removal tool 12.

Figure 2:
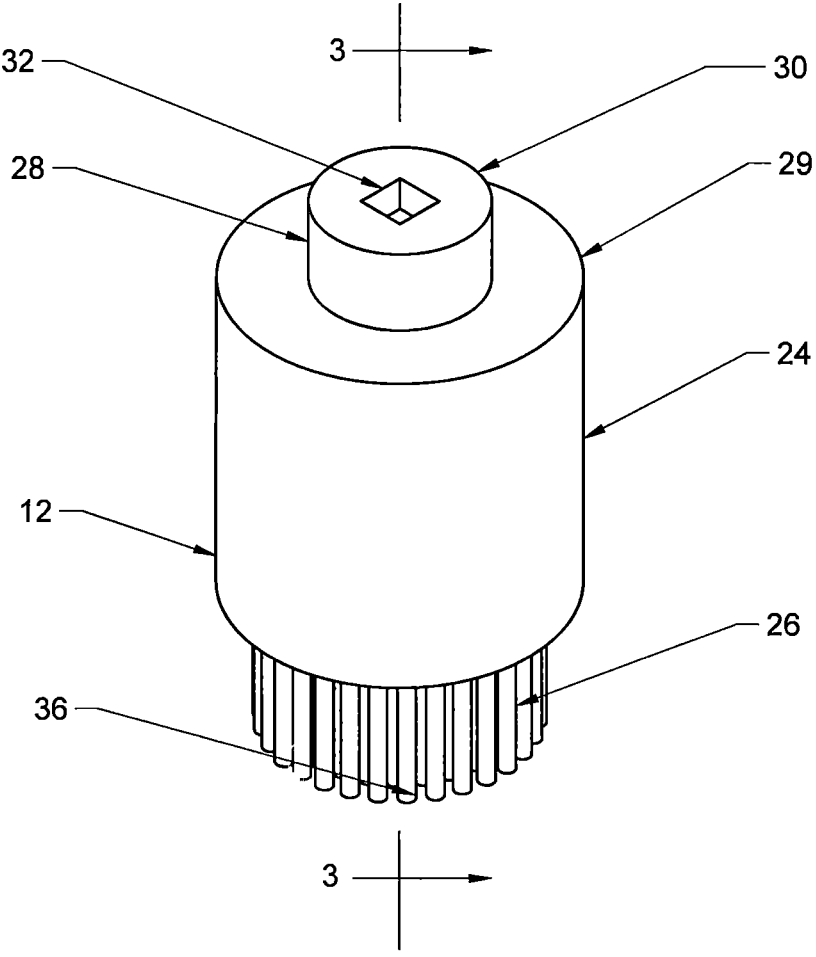

FIG. 2 is perspective view of a first embodiment of the epithelial removal tool 12 with a light emitter. The removal tool 12 has a housing 24 and brush 26 which has bristles that are fixedly secured to the housing. The bristles of the brush 26 together provide a removal member for removing epithelial tissue. The housing 24 has a top 28 with a flat annular-shaped region 29 and a chuck pin 30 which protrudes upward from the flat annular-shaped region 29. A rotary drive socket 32 is provided by a square shaped hole which is centrally formed into the upper-most end of the chuck pin 30. A light region is defined on a lower end 36 of the removal tool 12, at the terminal end of the brush 26.

FIG. 3 is a section view of the removal tool 12, taken along section line 3-3 of FIG. 2. Components for providing a light source are included in an upper portion of the housing 24. These components include an electric battery 38, a light source 40, a light collector 42, one or more optical fibers 44, and the switch 22. The light source 40 preferably includes an LED lamp. The switch 22 may be a manually operated switch or may be of the type which is operated by centrifugal force occurring when the removal tool 12 is rotated by the hand held motor unit 10. The light collector 42 is coupled to the optical fibers 44 and receives light from the light source 40 and transmits the light into the optical fibers 44.

The optical fibers 44 may in some embodiments be provided by the bristles of the brush 26, if capable of light transmission, and in other embodiments one or more optical fibers may be provided which are of different materials and sizes form the bristles of the brush 26. In some embodiments the optical fibers 44 may be shorter than the bristles of the brush 26 so that they do not touch the patients epithelial layer and yet are long enough to transmit light to the lower terminal end of the brush 26 and not disturb the overall rigidity of the individual bristles of the brush 26. In other embodiments the optical fibers 44 may, even though of different materials, be used integral with the bristles of the brush 26 for removing epithelial material. The bristles of the brush 26 are preferably formed of synthetic materials, but other materials may be used.

FIG. 4 is a section view of a second embodiment of an epithelial removal tool 12 with the light emitter having an external power source, as would be viewed when taken along section line 3-3 of FIG. 2. The transmitter adapter 20 is shown having one or more power coils 50 which emit magnetic fields to inductive coils 52. In yet other embodiments, the transmitter adapter 20 may emit light signals and components 52, rather then inductive coils, may be instead provided by power members which emit electric power in response to receiving light signals. A controller 54 is provided to regulate current and voltage applied to the lamp 56. The lamp 56 is preferably provided by an LED lamp. A light collector 58 is coupled to the optical fibers 44 for receiving light from the lamp 56 and passing the light to the optical fibers 44.

FIG. 5 is a section view of a third embodiment of an epithelial removal tool 12 with a light emitter having an external light source, as would be viewed when taken along section line 3-3 of FIG. 2. The transmitter adapter 20 of the third embodiment provides a light emitter 60, which may be provided by an electrically powered lamp or which itself may be the terminal end of one or more optical fibers guiding light from a light source mounted in a different position on the hand-held motor unit 10. One or more light collectors 10 are mounted to the top 28 of the housing 24, preferably at the annular shaped flat section 29. The one or more light collectors 10 may be protrude from, be flush with, or may be recesses into the top 28. The one ore more light collectors 10 are coupled to corresponding ones of the optical fibers 44. The optical fibers 44 act as light guides and extend to the lower terminal end 36 of removal tool 12 to define a light region 34 at the terminal end of the bristles of the brush 26.

In a fourth embodiment, the housing 24 of FIG. 5 may be provided by an annular-shaped ring for securing the bristles of the brush 26 in fixed position. A second end mounted ring may be used to provide a chuck pin 30. The light collectors 62 may be secured to the end mounted ring.

Figure 6:
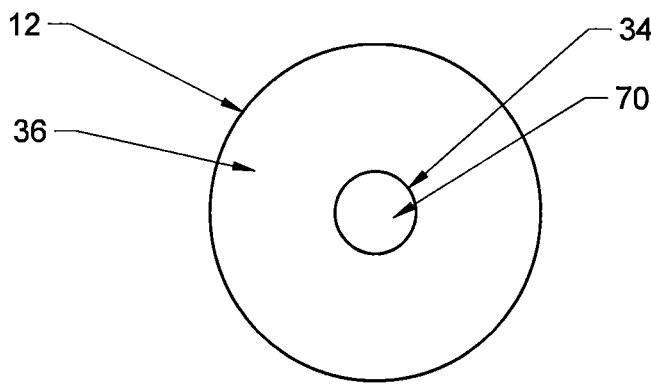

FIG. 6 is bottom view showing the lower end 36 of an epithelial removal tool 12 having a light emitter, and depicting the light region 34 from which the light is emitted as generally a point 70. The light region 34 provides a fixation light for the patient to focus on during surgery to prevent movement of the eye.

Figure 7:
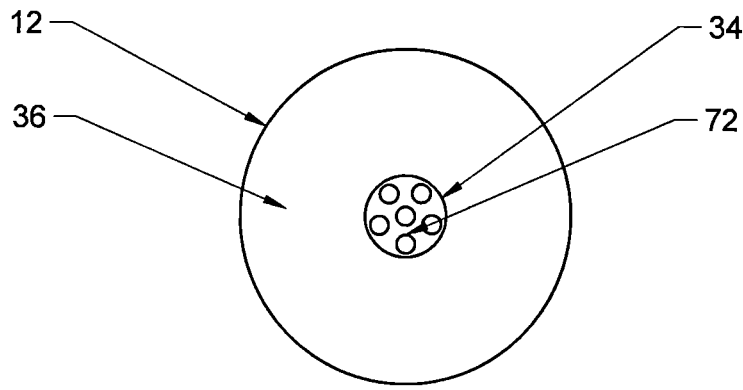

FIG. 7 is bottom view showing the lower end 36 of an epithelial removal tool 12 having a light emitter, and depicting the light region 34 from which the light is emitted as generally an annular-shaped region 72. It should be noted that the lower ends 36 are shown as having round-shaped peripheries, but other shapes may also be used, such as egg-shaped, oval, and other geometric shapes.

Figure 8:
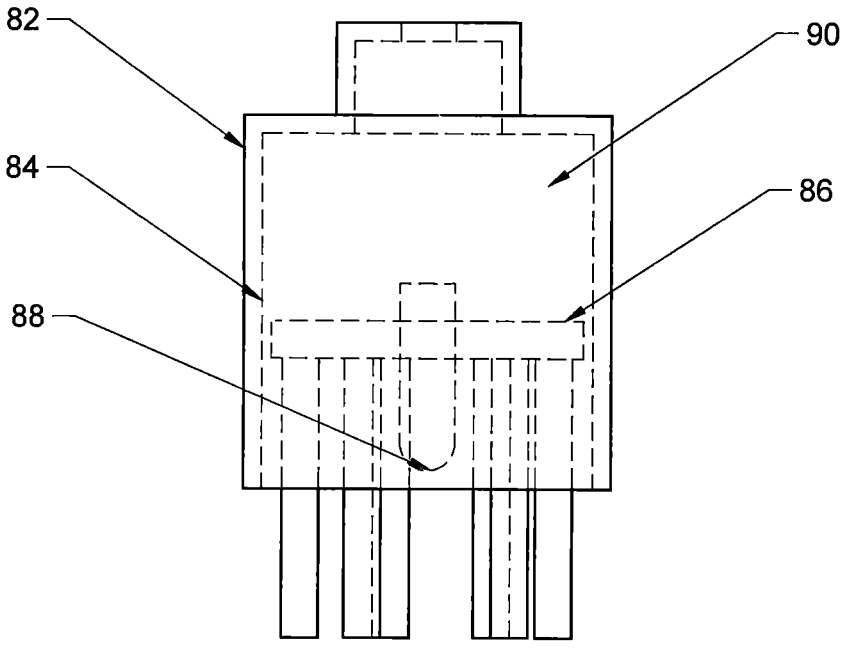

FIG. 8 is a section view of a fourth embodiment of an epithelial removal tool 82 having a light emitter, as would be viewed when taken along section line 3-3 of FIG. 2, and shows a single removal member 86 is formed of a solid material which protrudes from a housing 84. The single removal member 86 is preferably formed of a pliant material, which in some embodiments may be formed of a rubberized material. The pliant material forming the removal member 86 is preferably a polymeric material. As shown, an aperture 88 extends into the removal member 86 to transmit light to a lower surface 92. In some embodiments, the aperture 88 may be simply a blind hole ending slightly above the lower surface 92. In other embodiments the aperture 88 may be provided by one or more optical fibers which transmit the fixation light. In yet other embodiments, the aperture 88 in the removal member 86 may be omitted and the removal member 86 itself selected from a material which will transmit a sufficient amount of light to provide a fixation light for a patient. In the embodiment shown, and optical fiber extends from the removal member 86 and into the cavity 90 in the housing 84. Light inside the cavity 90 for transmitting through the removal member 86 may be provided by any of the embodiments described above in reference to FIGS. 2-7 and described below in reference to FIG. 9.

Figure 9:
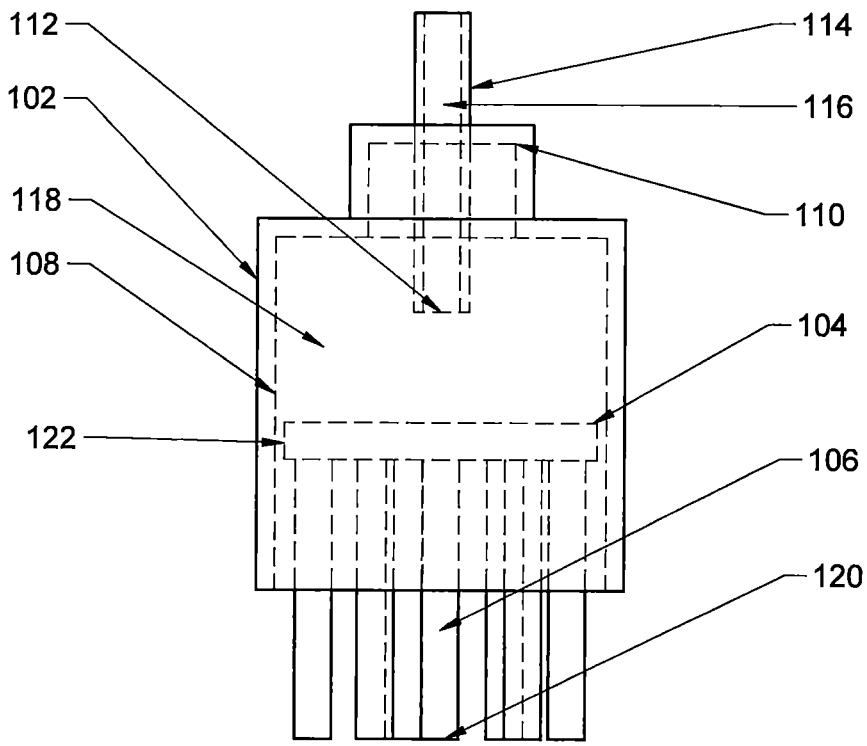

FIG. 9 is a section view of a fifth embodiment of an epithelial removal tool 102 having a light emitter which provides a fixation light, as would be viewed when taken along section line 3-3 of FIG. 2. An upper end is shaped to define a chuck pin 110. A light source is preferably located in the hand-held motor unit 10 and light is passed through the drive stem 114 of the motor unit 10. A light passage 116 may be provided by a hole through the drive stem 114 which transmits light or by an optical fiber. The drive stem 114 extends through a shaped aperture 112 corresponding to an end tip of the drive stem 114 and into a chamber 118 inside the removal tool housing 104. The shape aperture 112 preferably corresponds with the drive socket 32 of FIGS. 1-5 and 6. The walls 108 of the chamber 118 are silver in color to reflect light. A removal member 106 is fixed in the lower end of the housing 104 and the chamber 118. The removal member 106 is selected to transmit the light emitted form the drive stem 114 to the lower end 120 of the removal member 106. The removal member 106 may be formed of a single member, such as a pliant polymeric material as discussed above for removal member 86 of FIG. 8, or from brush bristles and optical fibers as discussed above for the removal member of FIGS. 2 through 7. The removal member 106 transmits the light to provide a fixation light for a patient to focus on to aid the patient in preventing eye movement during the surgical procedure to remove the epithelial material. An optional collector 122 is shown for transmitting light within the chamber 108 into the material of the removal member 106.

Figure 10:
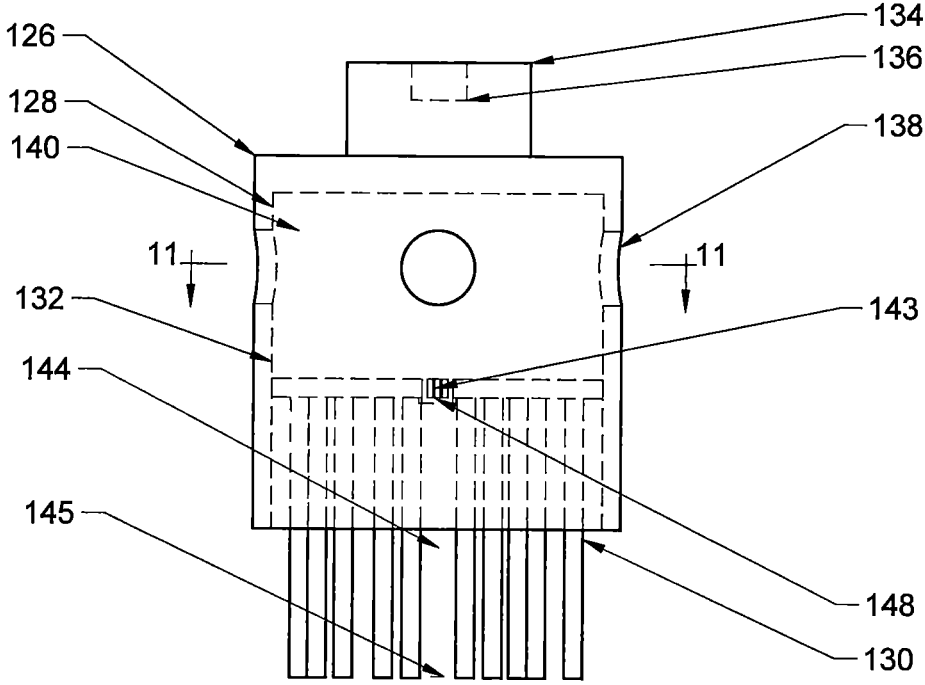

FIG. 10 is a section view of a sixth embodiment of an epithelial removal tool 126 having a light emitter which provides a fixation point 148, as would be viewed when taken along section line 3-3 of FIG. 2. The removal tool 126 has a housing 128 and removal member 130 which preferably extend circumferentially around a center line 150 defining a central longitudinal axis of the housing 128 and the removal member 130. The removal member 130 is provided by a brush which has bristles that are fixedly secured to the housing 128. The bristles of the brush extend to define a lower end of the removal member 130 which is moved across a patient's eye to remove epithelial tissue. The housing 128 has a top with a flat annular-shaped region and a centrally disposed chuck pin 134 which protrudes upward from the flat annular-shaped region. A rotary drive socket is provided by a shaped aperture 136 which is centrally formed into the upper-most end of the chuck pin 134. The housing 128 has side walls 132 which extend about and define a chamber 140 located on the interior of the housing 128. Light windows 138 are formed into the sidewalls 132 to pass ambient light from an exterior of the housing 128 into the chamber 140 located on the interior of the housing 128. The light windows 138 may be filled with a transparent or a translucent material which will pass light into the light guide 144, but which will seal the light windows 138 and prevent debris and impurities from begin captured in the housing and then being dispersed and contaminating a patient's eye. The chamber 140 may also be filled with such a transparent or translucent material. An optional collector 142 is shown for directing light into the light guide 144. The light guide 144 may be provided by one or more optical fibers which guide light collected at a first end 143 of the light guide 144 to emanate from a second end 145 of the light guide which defines the fixation point 148 located on the lower end of the removal member 130. The optical fibers of the light guide 144 may be provided by the bristles of the removal member 130, or by separate optical fibers.

Figure 11:
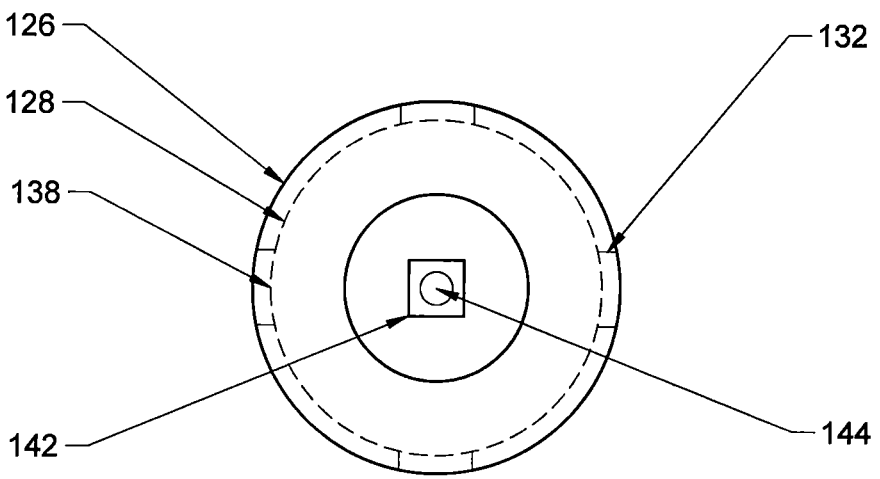

FIG. 11 is a section view of the epithelial removal tool 126, taken along section line 11-11 of FIG. 10. The housing 128 is shown with the four of the light windows 138 extending through the sidewall 132. A different number of light windows 138 may be cut through the sidewall 132, selecting a number and size of the light windows 138 to provide sufficient ambient light to pass through the light guide 144 and to the lower end of the removal member 130 defining the fixation point 148. The optional collector 142 is shown in phantom extending adjacent to the light guide 144. The collector 142 may in some embodiments be provided by an element which focuses light into the light guide 144, and in other embodiments may be provided by a horizontally extending disk having a centrally disposed aperture which passes light vertically into the light guide 144. Such an aperture in the light guide 144 may be configured to direct light into selected centrally disposed portions of the bristles of a brush providing the removal member 130.

Figure 12:
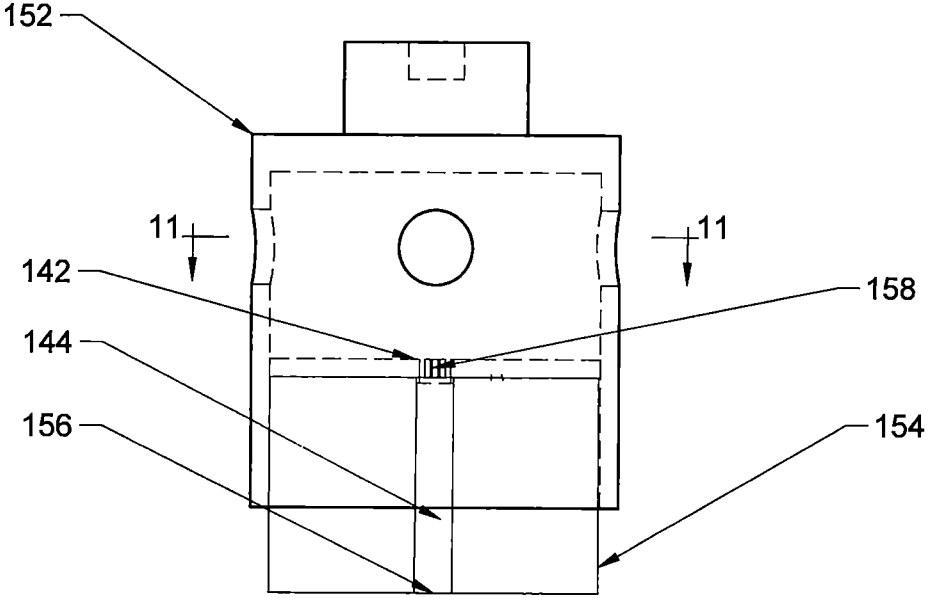

FIG. 12 is a section view of a seventh embodiment of an epithelial removal tool 152 having the same components as the epithelial removal tool 126, except that the removal member 130 formed of brush bristles to define a brush is replaced with removal member 154 formed of a single member, which is a pliant polymeric material. The light guide 144 is preferably provided by optical fibers which extend to the lower end 156 of the removal member 154 to define the fixation point 158. The collector 142 may in some embodiments be provided by an element which focuses light into the light guide 144, and in other embodiments may be provided by a horizontally extending disk having a centrally disposed aperture which passes light vertically into the light guide 144.

Figure 13:
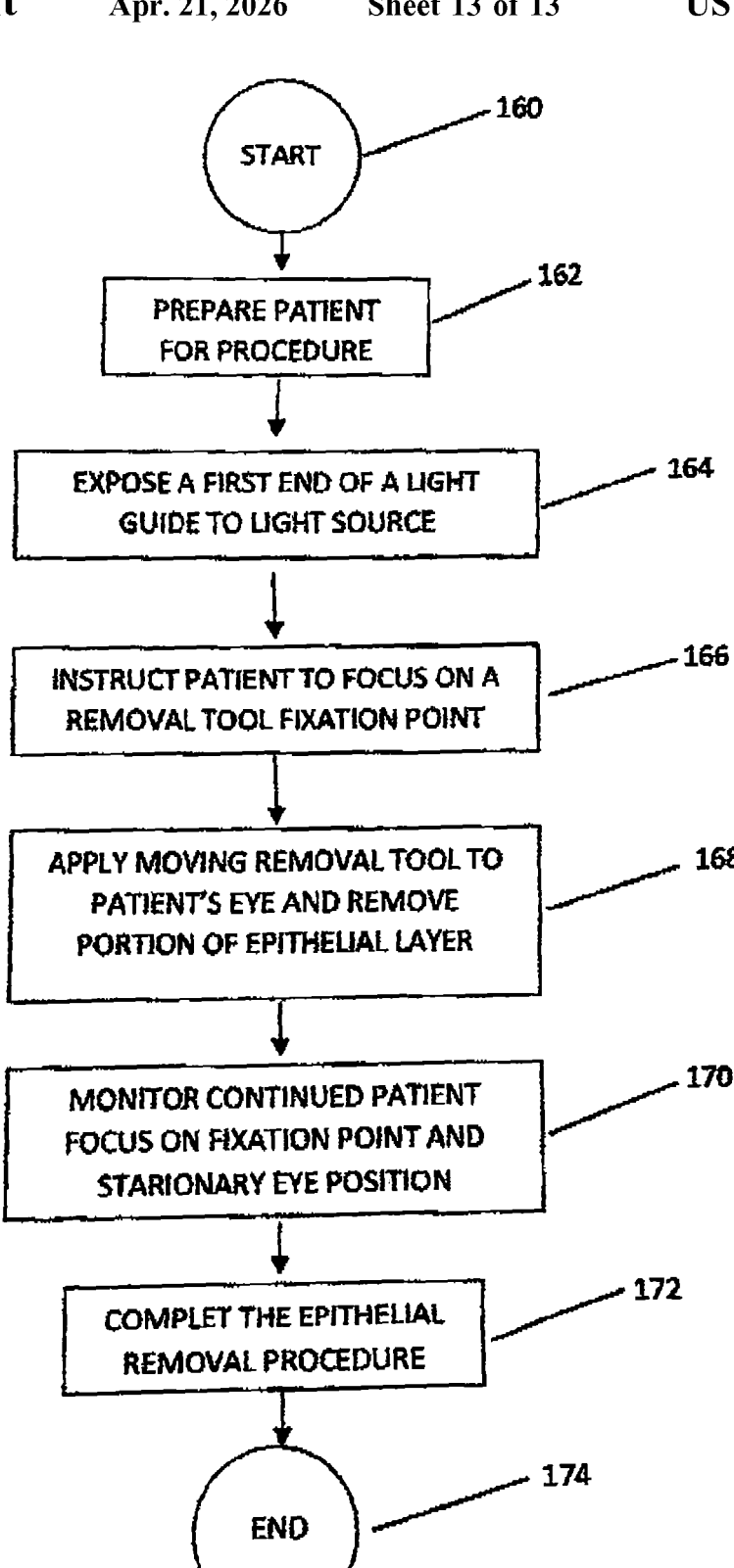

FIG. 13 is a flow chart illustrating a process for removal of epithelial material using one of the removal tools with light emitters according to the present invention. The process begins with the start step 160 and then proceeds to step 162. In step 162 the patient is prepared for the procedure and with patient's head disposed in a secured position for the procedure. In step 164 a first end of a light guide is exposed to a light source to emanate from a second end of the light guide to illuminate the fixation point disposed on the exterior, lower end of the removal member. The light guide extends through the removal member as discussed for the above-listed embodiments of removal tools, such that exposing the first end of the light guide causes light to emanate from the second end and define the fixation point located on the exterior, lower end of the removal member. The process then proceeds from step 164 to step 166 in which the patient is instructed to focus on the fixation point of the removal tool being utilized for the procedure. With the patient focusing on the fixation point to maintain his or her eye in a fixed position, the surgeon in step 168 will apply the moving removal tool to the patient's eye and remove a portion of the epithelial layer of the eye for purposes of correcting the patient's vision. The lower end of the removal tool, including the fixation point, is used to remove tissue from the epithelial layer of the patient's eye. In step 170 the surgeon continues the epithelial layer removal procedure while monitoring the patient's continued focus on the fixation point and the eye remaining in a stationary position. In step 170 the surgeon completes the removal procedure and the process ends in step 174.

It should be noted that the various removal members of FIGS. 1-12 may pass light across an entire lower surface, just a point as shown in FIG. 6, as a circle pattern as shown in FIG. 7, or across the entire lower surface as shown and described above for the lower surface 92 of the removal member 86 of FIG. 8 and the lower surface 120 of the removal member 106 of FIG. 9. Additionally, since the light being transmitted it not being used for illumination but rather to provide a fixation point for patients to focus on during surgery to aid in the patient preventing eye movement, the transmitted light need not be bright or intense. Since used for a fixation point and not illumination, the fixation light emitted need not shine but merely needs to glow. Patterns may also be formed into the material forming the removal members by, for example, regions or lines of dark color or various other colors, to define fixation points. The patterns may be provided by a layer which simply apply color, black or dark regions, which may be a layer on the upper surface or embedded within the removal member.

The housings shown in FIGS. 2-5 may have interior chambers similar to the chamber 90 of FIG. 8 and the chamber 118 of FIG. 9, or the corresponding regions of FIGS. 2-5 may have similar type chambers, or may be filled with a potting material or of the material from which the respective housings are formed, such the components disclosed above are embedded within the fill material. As discussed above for FIGS. 10-12, the potting material may be transparent or translucent for providing sufficient light to emanate from the lower end surfaces 146 and provide fixation points 148 and 158.

The present invention provides advantages of an epithelial removal tool and method for using the epithelial tool to provide a fixation light on which a patient may concentrate during ophthalmic surgery to prevent eye movement. One or more optical fibers extend through a removal member portion of the epithelial removal tool for passing light which is emitted at the terminal end which removes the epithelial tissue and the emitted light is visible to the patient during the procedure. In a first embodiment a light source and power supply are provided on board the removal tool. In a second embodiment a light source is provide on board the removal tool, and a power source is provided external of the removal tool. In a third embodiment the light source and power source are located external of the removal tool, and a collector is mounted to the removal tool for passing light from the light source to the one or more optical fibers.

Although the preferred embodiment has been described in detail, it should be understood that various changes, substitutions and alterations can be made therein without departing from the spirit and scope of the invention as defined by the appended claims.

What is claimed is:

1. A method for an ophthalmic surgical procedure to remove tissue from an epithelial layer of an eye for correcting a patient's vision, the method comprising the steps of:
    providing an epithelial removal tool having a removal member and a light guide, wherein the light guide has a first end and a second end, and extends through the removal member to a lower end of the removal member for passing light from the first end to the second end disposed on the lower end of the removal member;

mounting the epithelial removal tool to a motor unit which provides motion to the lower end of the removal member to remove the tissue from the epithelial layer of the eye;
    preparing the patient for the procedure;
    exposing the first end of the light guide to a light source, which causes light from the light source to emanate from the second end of the light guide and the lower end of the removal member, defining a fixation point disposed on the lower end of the removal member;
    instructing the patient to focus on the fixation point disposed on the lower end of the removal member of the epithelial removal tool;
    applying the removal member to the patient's eye while the motor unit moves the epithelial removal tool to move the lower end of the removal member and removes the tissue from the epithelial layer of the patient's eye; and
    monitoring the patient's stationary eye position and continued focus on the fixation point located disposed on the lower end of the removal tool while removing the tissue from the epithelial layer with the lower end of the removal member.

2. The method according to claim 1, wherein the step of exposing the first end of the light guide to a light source comprises exposing an exterior of the epithelial removal tool to ambient light in proximity to the patient.

3. The method according to claim 1, wherein the step of exposing the first end of the light guide to a light source comprises providing the light source and a power supply interiorly within the epithelial removal tool and applying the power supply to the light source.

4. The method according to claim 1, wherein the step of exposing the first end of the light guide to a light source comprises mounting the first end of the light guide to an upper end of the epithelial removal tool and mounting the light source and a power supply on the motor unit, with the light source configured for illuminating the first end of the light guide.

5. The method according to claim 1, wherein the step of providing an epithelial removal tool having a removal member and a light guide comprises providing the removal member as brush bristles which are coupled together to define a brush end.

6. The method according to claim 5, wherein said light guide is provided by one or more optical fibers defined by a portion of said brush bristles.

7. The method according to claim 1, wherein the step of providing an epithelial removal tool having a removal member and a light guide comprises forming the removal member of a solid, pliant material.

8. The method according to claim 7, wherein said pliant material is formed of a polymeric material.

9. A method for an ophthalmic surgical procedure to remove tissue from an epithelial lawyer of an eye for correcting a patient's vision, the method comprising the steps of:
    providing an epithelial removal tool having a removal member and a light guide, wherein the light guide has a first end and a second end, and extends through the removal member to a lower end of the removal member for passing light from the first end to the second end disposed on the lower end of the removal member;
    mounting the epithelial removal tool to a motor unit which provides rotary motion to the lower end of the removal member to remove the tissue from the epithelial layer of the eye;

preparing the patient for the procedure;

exposing the first end of the light guide to a light source, which causes light from the light source to emanate from the second end of the light guide and the lower end of the removal member, defining a fixation point disposed on the lower end of the removal member;

instructing the patient to focus on the fixation point disposed on the lower end of the removal member of the epithelial removal tool;

applying the removal member to the patient's eye while the motor unit rotates the epithelial removal tool to rotate the lower end of the removal member and removes the tissue from the epithelial layer of the patient's eye; and monitoring the patient's stationary eye position and continued focus on the fixation point located disposed on the lower end of the removal tool while removing the tissue from the epithelial layer with the lower end of the removal member.

10. The method according to claim 9, wherein the step of exposing the first end of the light guide to a light source comprises exposing an exterior of the epithelial removal tool to ambient light in proximity to the patient.

11. The method according to claim 9, wherein the step of exposing the first end of the light guide to a light source comprises providing the light source and a power supply interiorly within the epithelial removal tool and applying the power supply to the light source.

12. The method according to claim 9, wherein the step of exposing the first end of the light guide to a light source comprises mounting the first end of the light guide to an upper end of the epithelial removal tool and mounting the light source and a power supply on the motor unit, with the light source configured for illuminating the first end of the light guide.

13. The method according to claim 9, wherein the step of providing an epithelial removal tool having a removal member and a light guide comprises providing the removal member as brush bristles which are coupled together to define a brush end.

14. The method according to claim 13, wherein said light guide is provided by one or more optical fibers defined by a portion of said brush bristles.

15. The method according to claim 9, wherein the step of providing an epithelial removal tool having a removal member and a light guide comprises forming the removal member as a solid, pliant material.

16. The method according to claim 15, wherein said pliant material is formed of a polymeric material.

* * * * *